United States Patent
Rousseau et al.

(10) Patent No.: US 8,206,632 B2
(45) Date of Patent: Jun. 26, 2012

(54) METHODS OF MAKING COMPOSITE PROSTHETIC DEVICES HAVING IMPROVED BOND STRENGTH

(75) Inventors: Robert A. Rousseau, Ottsville, PA (US); Tara Zabrosky, Millstone Township, NJ (US)

(73) Assignee: Ethicon, Inc., Somerville, NJ (US)

( * ) Notice: Subject to any disclaimer, the term of this patent is extended or adjusted under 35 U.S.C. 154(b) by 4 days.

(21) Appl. No.: 11/959,244

(22) Filed: Dec. 18, 2007

(65) Prior Publication Data

US 2009/0152766 A1 Jun. 18, 2009

(51) Int. Cl.
*B29C 65/00* (2006.01)

(52) U.S. Cl. ........ 264/258; 264/241; 264/261; 264/319; 264/320; 264/257; 156/308.6; 156/308.8; 606/151; 623/23.72; 623/23.74

(58) Field of Classification Search .................. 264/261, 264/241, 257, 258, 319, 320; 606/151; 623/23.76, 623/23.72, 23.74; 128/899, 96.1; 156/308.6, 156/308.8
See application file for complete search history.

(56) References Cited

U.S. PATENT DOCUMENTS

| | | | |
|---|---|---|---|
| 3,467,566 A | 9/1969 | Conti | |
| 4,144,376 A * | 3/1979 | Beckmann et al. | 428/429 |
| 4,453,997 A * | 6/1984 | Hori et al. | 156/305 |
| 4,906,497 A * | 3/1990 | Hellmann et al. | 428/49 |
| 4,908,167 A | 3/1990 | Beckmann et al. | |
| 5,002,551 A | 3/1991 | Linsky et al. | |
| 5,007,916 A | 4/1991 | Linsky et al. | |
| 5,092,884 A | 3/1992 | Deveraux et al. | |
| 5,254,133 A | 10/1993 | Seid | |
| 5,578,046 A | 11/1996 | Liu et al. | |
| 5,593,441 A | 1/1997 | Lichtenstein et al. | |
| 5,626,611 A | 5/1997 | Liu et al. | |
| 5,634,944 A | 6/1997 | Magram | |
| 5,686,090 A * | 11/1997 | Schilder et al. | 424/423 |
| 5,695,525 A | 12/1997 | Mulhauser et al. | |
| 5,725,577 A | 3/1998 | Saxon | |
| 5,743,917 A | 4/1998 | Saxon | |
| 5,766,246 A | 6/1998 | Mulhauser et al. | |
| 5,791,352 A | 8/1998 | Reich et al. | |
| 5,990,378 A | 11/1999 | Ellis | |
| 6,031,148 A | 2/2000 | Hayes et al. | |
| 6,093,200 A | 7/2000 | Liu et al. | |
| 6,120,539 A | 9/2000 | Eldridge et al. | |

(Continued)

FOREIGN PATENT DOCUMENTS

CA 2114282 7/1994

(Continued)

*Primary Examiner* — Christina Johnson
*Assistant Examiner* — Saeed Huda

(57) ABSTRACT

A method of making a composite prosthetic device, such as a hernia repair device, includes providing a support layer, juxtaposing a layer of an absorbable material with the support layer, and disposing an absorbable adhesive between the support layer and the layer of an absorbable material. The method includes heating the layers for melting the absorbable adhesive so as to bond the support layer with the layer of the absorbable material. Before the heating step, the moisture content of at least one of the layers is increased for improving thermal conductivity between the layers so as to enhance the strength of the bonds formed between the layers. The moisture content may be increased by exposing at least one of the layers to an environment having elevated relative humidity. In one embodiment, the support layer is polypropylene mesh, the layer of the absorbable material is oxidized regenerated cellulose, and the absorbable adhesive is polydioxanone.

25 Claims, 7 Drawing Sheets

U.S. PATENT DOCUMENTS

| | | | |
|---|---|---|---|
| 6,162,962 A | 12/2000 | Hinsch et al. | |
| 6,258,124 B1 | 7/2001 | Darois et al. | |
| 6,264,702 B1 | 7/2001 | Ory et al. | |
| 6,270,530 B1 | 8/2001 | Eldridge et al. | |
| 6,294,202 B1 | 9/2001 | Burns et al. | |
| 6,319,264 B1 | 11/2001 | Tormala et al. | |
| 6,383,201 B1 | 5/2002 | Dong | |
| 6,447,551 B1 | 9/2002 | Goldmann | |
| 6,451,032 B1 | 9/2002 | Ory et al. | |
| 6,703,041 B2 | 3/2004 | Burns et al. | |
| 6,737,371 B1 | 5/2004 | Planck et al. | |
| 6,800,082 B2 | 10/2004 | Rousseau | |
| 6,966,918 B1 | 11/2005 | Schuldt-hempe et al. | |
| 2002/0018813 A1 | 2/2002 | Burns et al. | |
| 2002/0052654 A1 | 5/2002 | Darois et al. | |
| 2002/0131933 A1* | 9/2002 | Delmotte | 424/1.11 |
| 2002/0143403 A1 | 10/2002 | Vaidyanathan et al. | |
| 2003/0040809 A1 | 2/2003 | Goldmann et al. | |
| 2003/0078602 A1 | 4/2003 | Rousseau | |
| 2003/0100955 A1* | 5/2003 | Greenawalt et al. | 623/23.74 |
| 2003/0120745 A1 | 6/2003 | Katagishi et al. | |
| 2004/0091504 A1* | 5/2004 | Hamann | 424/195.17 |
| 2005/0010306 A1 | 1/2005 | Priewe et al. | |
| 2005/0113849 A1* | 5/2005 | Popadiuk et al. | 606/151 |
| 2006/0258995 A1 | 11/2006 | Pendharkar | |
| 2007/0208365 A1 | 9/2007 | Lee et al. | |
| 2008/0147200 A1 | 6/2008 | Rousseau et al. | |

FOREIGN PATENT DOCUMENTS

| | | |
|---|---|---|
| DE | 3830005 | 11/1989 |
| EP | 0868999 A2 | 10/1998 |
| EP | 1541183 A1 | 6/2005 |
| WO | 0016822 | 3/2000 |

* cited by examiner

MOISTURE REGAIN (ORC)

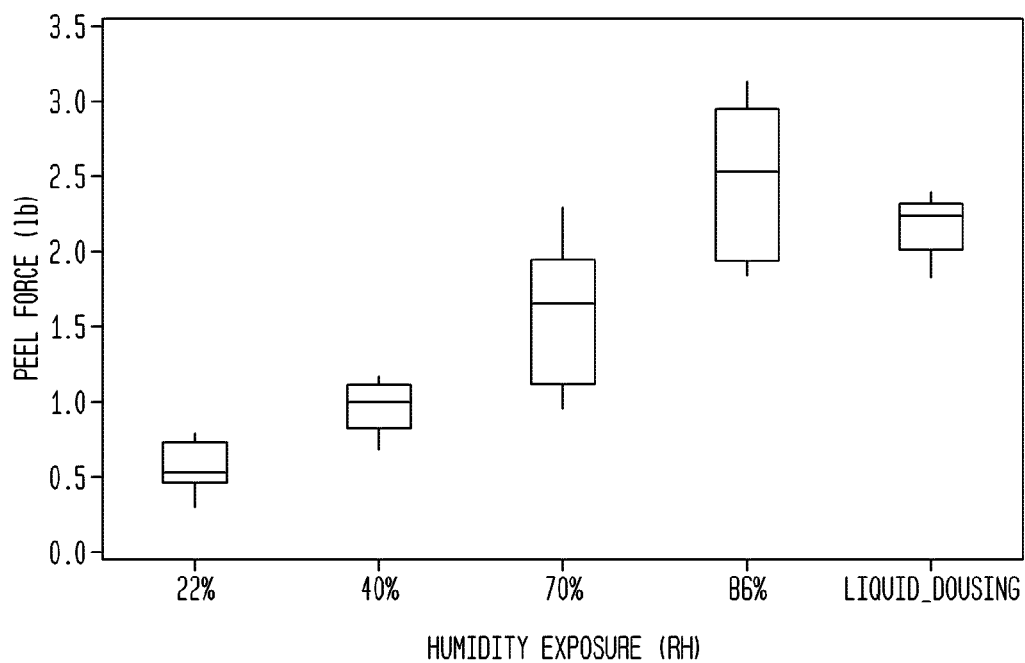
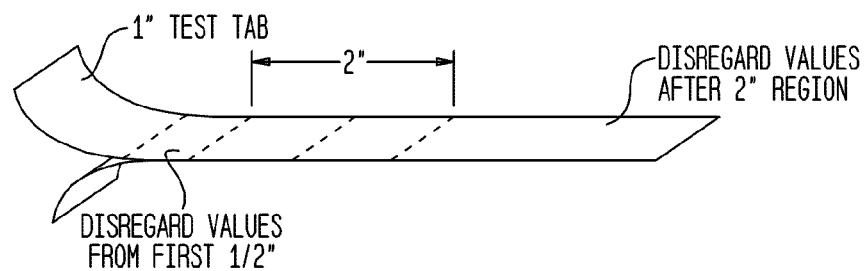

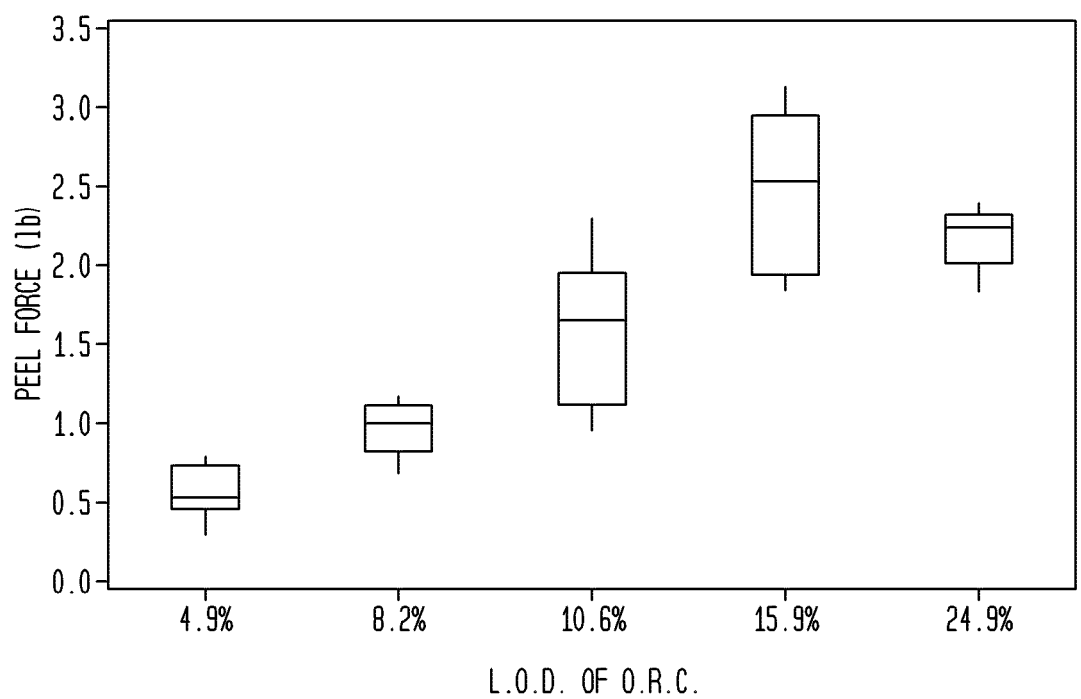

METHODS OF MAKING COMPOSITE PROSTHETIC DEVICES HAVING IMPROVED BOND STRENGTH

BACKGROUND OF THE INVENTION

1. Field of the Invention

The present invention generally relates to implantable prosthetic devices, and more specifically relates to composite prosthetic devices having layers with improved bond strength.

2. Description of the Related Art

It is generally known to use multilayered or composite fabrics in connection with medical procedures. For example, composite fabrics may be used as all purpose pads, wound dressings, surgical meshes, hernia repair meshes, adhesion prevention meshes, tissue reinforcement meshes, defect closure devices, and hemostats.

When treating hernias, one conventional, widely-used surgical procedure involves transferring the hernia content back into the abdomen, and then using sutures to close the abdominal wall opening. When using the above-described conventional procedure, however, a hernial relapse occurs about 20% of the time.

Due to the high relapse rate following conventional hernia operations, many hernia procedures now use artificial implants for reconstructing the abdominal wall. These artificial implants generally include an open mesh material, such as polypropylene or polyester. After implantation, the ideal prosthetic device is incorporated by the surrounding tissue to form a firm connection between the implant and the abdominal wall, does not promote adhesions, has pliability, and provides appropriate strength.

In many instances, artificial implants used for reinforcing the abdominal wall and covering abdominal wall defects are made of multiple layers of a non-absorbable, porous material and an absorbable anti-adhesion material. One multi-layered prosthetic device having a polypropylene mesh, such as that sold under the trademark Marlex®, and an absorbable film, such as that sold under the trademark Gelfilm®, is described by Jenkins et al., in "A Comparison of Prosthetic Materials Used to Repair Abdominal Wall Defects", Surgery, Vol. 94, No. 2, August 1983, pp. 392-398.

There have been other efforts directed to providing composite or multi-layered prosthetic devices that are efficiently absorbed into a body. For example, commonly assigned U.S. Patent Application Publication No. US 2005/0113849 to Popadiuk et al., the disclosure of which is hereby incorporated by reference herein, discloses a prosthetic repair device including a non-absorbable material, a first absorbable material having a first absorption rate, and a second absorbable material having a faster absorption rate than the first absorption rate. Another embodiment is directed to a prosthetic repair device having a non-absorbable, porous material that is encapsulated with a first absorbable component, and a second absorbable material having a faster absorption rate than the first absorbable component. The prosthetic repair devices described in the '849 publication are designed to exhibit strength and pliability, while efficiently incorporating surrounding tissue at an impressive rate.

U.S. Pat. No. 5,593,441 to Lichtenstein discloses a composite prosthesis and methods for limiting the incidence of postoperative adhesions. The composite includes a mesh fabric and a barrier that prevents exposure of the mesh fabric to areas of potential adhesion. The interstices of the mesh fabric are infiltrated by tissue which secures the prosthesis in place. The composite is positioned with the barrier relative to the region where adhesions may occur, such as the abdominal viscera.

Commonly assigned U.S. Pat. No. 5,686,090 to Schilder et al., the disclosure of which is hereby incorporated by reference herein, teaches a multilayered prosthetic device. The layers of the device are bonded together using materials having different melting points. During manufacture, the implant is heated to a temperature which is higher than the melting point of the material with the lower melting point, but below the melting point of the material with the higher melting point so that one of the layers melts and combines with the adjoining layer. In one embodiment, a film made from a material having a lower melting point is placed between two layers having different melting points. The structure is heated so that the film melts and becomes porous and the two layers are bonded to each other.

Commonly assigned U.S. Patent Application Publication No. US 2005/0010306 to Priewe et al., the disclosure of which is hereby incorporated by reference herein, discloses an Areal implant having a stable, mesh-like base structure having pores of a size in the range from 1.5 mm to 8 mm. The implant includes a synthetic, resorbable polymer film on each of two opposing surfaces. The two polymer films are glued or welded together in pores of the basic structure.

In many instances, the layers of a composite prosthetic device are connected or bonded together using an adhesive. The layers may be bonded together by heating the adhesive to a temperature higher than the melting point of the adhesive. The melted adhesive then flows into the adjacent layers for bonding the layers together. If the heat applied to the device is insufficient to completely melt the adhesive disposed therein, then weak bonding of the layers may result. This problem is particularly likely to occur when laminating multiple layers of absorbable films with mesh structures having poor heat transfer properties.

In spite of the above advances, there remains a need for improved composite prosthetic devices having strength and pliability, and that minimize the likelihood of adhesions forming between the device and the surrounding tissue. Moreover, there remains a need for prosthetic devices having improved bond strength between the layers so that the layers do not pull apart or delaminate. There also remains a need for methods for effectively conducting heat through composite prosthetic devices for effectively melting the adhesive to properly fuse or bond the layers together.

SUMMARY OF THE INVENTION

The present invention provides multilayered or composite prosthetic implants having improved strength. In one embodiment, the layers of a prosthetic device are laminated together using improved lamination techniques that strengthen the bonds between the layers to minimize the likelihood that the layers will pull apart during use. In one embodiment, the multilayered prosthetic implant is a prosthetic repair device such as a hernia repair device.

In one embodiment of the present invention, a method of making a composite prosthetic device includes providing a support layer, juxtaposing a layer of an absorbable material with the support layer, and disposing an absorbable adhesive between the support layer and the layer of an absorbable material. The method may include heating the layers for melting the absorbable adhesive so as to bond the support layer with the layer of an absorbable material, and before the heating step, increasing the moisture content of at least one of the layers for improving thermal conduction between the layers. In one embodiment, pressure may be applied during the heating step such as by using pressure-applying platens or rollers.

In one embodiment of the present invention, the moisture content of at least one of the layers is increased. The moisture content may be increased by exposing at least one of the layers to an environment having an elevated relative humidity level. The exposing step may include placing at least one of the layers inside an enclosed area that has the elevated humidity level relative to ambient conditions. In one embodiment, the moisture content of any one of the layers used in the composite device may be increased prior to the heating step. Layers subjected to increased moisture content may include any one of the support layer, the absorbable adhesive, the layer of an absorbable material, and the release liners. In one embodiment, at least one of the layers is exposed to the elevated humidity level for at least one minute and more preferably at least one hour before the heating step. In one embodiment, at least one of the layers is exposed to the elevated humidity level for about two hours before the heating step. The elevated humidity level is preferably between about 40-90% relative humidity and more preferably between about 70-86% relative humidity.

In one embodiment, the moisture of one or more of the layers may be increased during a lamination step. For example, the layers of the laminate may be assembled together for lamination, and liquid, moisture, or steam may be introduced to one or more of the layers as pressure and/or heat is applied to the stacked layers. In one embodiment, the moisture may be introduced by the tools used to apply the pressure and/or heat to the layers. In one embodiment, the platens or rollers used to press the layers may have openings for introducing water, moisture, or steam to the stacked layers. As noted above, the increased moisture content preferably enhances thermal conductivity through the device during lamination so as to improve the bond strength of the laminated device.

The support layer may include a non-absorbable material such as a polypropylene mesh, or a partly absorbable material including an absorbable component and a non-absorbable component. The layer of an absorbable material may include a cellulose fabric such as oxidized regenerated cellulose. The absorbable adhesive may include one or more polydioxanone films.

Although the present invention is not limited by any particular theory of operation, it is believed that introducing moisture into one or more layers of a composite assembly prior to or during a lamination step will improve thermal conductivity between the layers of the assembly. The enhanced thermal conductivity increases the likelihood that the adhesive materials used to bond the layers of the assembly together will melt more completely so as to form stronger bonds between the layers. The improved bond strength between the layers will, in turn, improve the reliability of the prosthetic device.

In one embodiment, the layers of the composite assembly are not doused in a liquid such as water. As discussed herein, it has been determined that liquid dousing of one or more of the layers prior to or during lamination may actually reduce the strength of the bonds that may be formed between the layers. Thus, the present invention seeks to increase the moisture content of at least one of the layers to a level that is short of a liquid dousing level. This may be accomplished by exposing one or more of the layers of the composite assembly to elevated humidity levels prior to applying heat and/or pressure during a lamination stage, or while applying the pressure and/or heat during a lamination step. The preferred humidity levels to which the one or more layers may be exposed are about 40%-90%, and more preferably about 70%-86%. The period of exposure to elevated humidity is preferably at least one minute, more preferably at least one hour, and even more preferably about two hours.

In one embodiment, further significant improvements in bond strength are not obtained by exposing the layers to elevated humidity for more than about two hours. Thus, the present invention provides an unexpected result in that the optimum period for exposure of the at least one layer to elevated humidity levels is about two hours. Any further gains made by exposing the layers to elevated humidity for more than two hours are offset by efficiency losses resulting from longer production times.

In one embodiment of the present invention, a method of making a composite prosthetic device includes providing a support layer, juxtaposing a layer of an absorbable, anti-adhesion material with the support layer, and disposing an absorbable adhesive between the support layer and the layer of an absorbable, anti-adhesion material. In one embodiment, the support layer is polypropylene mesh, the absorbable, anti-adhesion material is cellulose fabric such as oxidized regenerated cellulose, and the absorbable adhesive is a polydioxanone film.

The method desirably includes heating the absorbable adhesive for bonding the support layer with the layer of an absorbable, anti-adhesion material. In one embodiment, prior to the heating step, the moisture content of at least one of the layers is increased for improving thermal conductivity between the layers during the heating step. In one embodiment, pressure may also be applied to the composite structure during the heating step. In highly preferred embodiments, the heat and pressure are provided simultaneously. The moisture content may be increased by storing at least one of the layers inside an enclosed area having an elevated humidity level for at least one minute, more preferably at least one hour, and even more preferably for about two hours. The at least one of the layers exposed to the elevated humidity is desirably removed from the enclosed area prior to the laminating step. In one embodiment, the at least one of the layers is removed from the enclosed area immediately prior to the laminating step (e.g. seconds before).

In one embodiment, a second absorbable adhesive may be provided over a surface of the support layer that faces away from the layer of an absorbable, anti-adhesion material. The support layer may have a plurality of openings extending therethrough and the absorbable adhesives may flow into openings in the support layer. When heated, the absorbable adhesive may flow into openings in the support layer for forming a protective, absorbable barrier or coating that covers at least one of the first and second major surfaces of the support layer. In one embodiment, after the prosthetic device is implanted, the absorbable adhesive barrier initially remains in place to prevent adhesions forming with the support layer. After a period of time, however, the absorbable adhesive barrier will recede to expose the plurality of openings in the support layer, which will allow tissue to grow into the support layer.

In one embodiment of the present invention, a method of making a composite prosthetic device includes assembling a multilayered structure with a first support layer having a first surface and a second surface, a second layer of an absorbable adhesive overlying the first surface of the first support layer, a third layer of an absorbable adhesive overlying the second surface of the first support layer, and a fourth layer of an absorbable material overlying the third layer of an absorbable adhesive. In one embodiment, the first support layer includes polypropylene, the second and third layers of the absorbable adhesive include polydioxanone, and the fourth layer of the absorbable material includes cellulose fabric, such as oxidized regenerated cellulose.

In one embodiment of the present invention, the method desirably includes heating the assembled multilayer structure to melt the second and third layers of an absorbable adhesive so as to bond the first and fourth layers together, and prior to the heating step, increasing the moisture content of at least one of the layers for improving thermal conductivity throughout the assembled multilayer structure during the heating step. In one embodiment, pressure and/or heat may be applied to the multilayer structure such as by using platens or rollers.

In one embodiment, the first support layer has openings therein, and the absorbable adhesive flows into the openings during the heating step to form an absorbable barrier that coats the first and second surfaces of the support layer. After implantation of the prosthetic device, the absorbable barrier may recede to expose the openings so that tissue may grow into the openings.

In one embodiment, the moisture content of one or more of the layers may be increased by exposing the fourth layer of an absorbable material to an elevated humidity level prior to the heating step. This may be accomplished by exposing at least one of the layers to an environment having an elevated relative humidity level for at least one minute, more preferably for at least one hour, and even more preferably for about two hours. The exposing step may include storing at least one of the layers inside the environment having the elevated relative humidity level, and removing the at least one of the layers from the environment prior to the assembling and heating steps. The elevated relative humidity level may be between about 40-90% relative humidity, and more preferably between about 70-86% relative humidity.

In one embodiment of the present invention, the method may include, prior to the heating and pressure steps, disposing a first release liner over the second layer of an absorbable adhesive and a second release liner over the fourth layer of an absorbable material. The release liners may be made of releasable paper such as the release liners sold under the trademark TEKKOTE.

In one embodiment, a method of laminating two layers of material to form a composite medical device includes placing at least a portion of a first layer in contact with a portion of a second layer to form an assembly, and heating the assembly in the presence of a volatile media, such as water or IPA, to a temperature greater than the boiling point of the volatile media and sufficient to fuse the layers together. The method may be particularly suitable for use in the lamination of oxidized regenerated cellulose with polypropylene fabric and PDS film.

These and other preferred embodiments of the present invention will be described in more detail below.

BRIEF DESCRIPTION OF THE DRAWING

FIG. 3 is a graph showing the peel force required to separate two layers of material versus humidity exposure, in accordance with one embodiment of the present invention.

FIG. 4 shows one step of a test used for determining the peel force required to separate two layers, in accordance with one embodiment of the present invention.

FIG. 5 is a graph showing the peel force required to separate two layers versus a loss on drying value, in accordance with one embodiment of the present invention.

DETAILED DESCRIPTION

Figure 1:
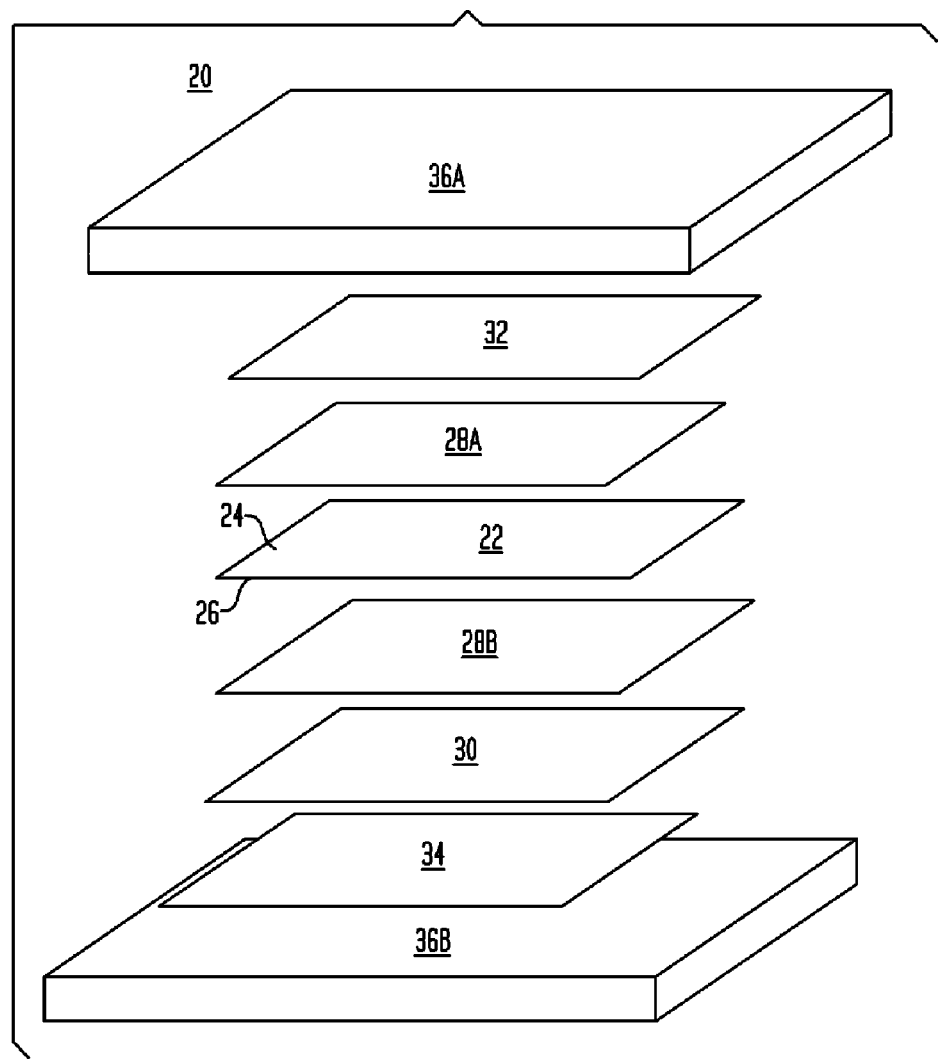
FIG. 1 shows an exploded view of a composite prosthetic device, in accordance with one embodiment of the present invention.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Referring to FIG. 1, in one embodiment of the present invention, a composite prosthetic device 20 includes a support layer 22 having a first major surface 24 and a second major surface 26. The support layer 22 is preferably adapted to permit the anchoring of the composite prosthetic device to body parts such as the peritoneum or an abdominal wall. In one embodiment, after the composite prosthetic device is positioned over a body part, the support layer 22 desirably allows tissue infiltration into the composite prosthetic device. The support layer 22 may be open cell foam, a non-woven or woven structure including but not limited to a fabric, a mesh, a knit, a weave or a carded web, or a porous membrane. In certain preferred embodiments, the support layer 22 may be any biologically compatible and implantable synthetic or natural material that includes but is not limited to polyolefins such as polyethylene or polypropylene, polyesters, fluorpolymers such as polytetrafluoroethylene, polyamides such as nylon, and combinations thereof. In more preferred embodiments, the support layer may be one or more of a polypropylene mesh sold under the trademarks Prolene® and Marlex® by Ethicon, Inc. of Somerville, N.J. Other more preferred support layers may include a partly absorbable layer having a non-absorbable component and an absorbable component such as the support layers sold under the trademarks VYPRO and ULTRAPRO® by Ethicon, Inc. of Somerville, N.J.

The composite prosthetic device desirably includes an absorbable adhesive used to hold the layers of the device together. In one embodiment, the absorbable adhesive includes a first absorbable adhesive film 28A and a second absorbable adhesive film 28B. The first absorbable adhesive film 28A desirably overlies the first major surface 24 of the support layer 22, and the second absorbable adhesive film 28B desirably overlies the second major surface 26 of the support layer 22. In one embodiment, the first and second absorbable adhesive films 28A, 28B are preferably made of the same material. In certain preferred embodiments, the first and second absorbable adhesive films 28A, 28B may be made of but not limited to polydioxanone such as poly(1,4-dioxan-2-one), polymers or copolymers of organic hydroxyesters, polyglycolide, polylactide, polyhydroxy butyric acid, polycaprolactone, polytrimethylene carbonate and polyvinyl alcohol.

In one embodiment of the present invention, the absorbable adhesive may be heated so that the absorbable adhesive melts and flows into openings in the support layer 22. Thus, in certain embodiments, the first and second absorbable adhesive films 28A, 28B may encapsulate at least one of the first and second surfaces 24, 26 of the support layer 22. In one embodiment, the first absorbable adhesive film 28A has a thickness of about 0.1-1.2 mil over the first major surface 24 of the support layer 22, and the second absorbable adhesive film 28B has a thickness of about 0.1-1.2 mil over the second major surface 26 of the support layer 22. In one embodiment, the first absorbable adhesive film 28A has a thickness of about 0.1-0.5 mil and more preferably about 0.2 mil, and the second absorbable adhesive film 28B has a thickness of about 0.5-1.0 mil and more preferably about 0.8 mil.

The composite prosthetic device 20 also desirably includes a layer of an absorbable material 30 that is desirably laminated to the support layer 22 using at least one of the first and second absorbable adhesive films 28A, 28B. In certain preferred embodiments, the layer of an absorbable material 30 may be made of materials including but not limited to absorbable adhesion barriers such as the oxidized regenerated cellulose (ORC) fabric sold under the trademark Interceed®, cellulose fabric, gelatin films such as the Gelfilm® absorbable film, and polymers or copolymers of organic hydroxyesters, polyglycolide, polylactide, polydioxanone, polyhydroxy butyric acid, polycaprolactone, polytrimethylene carbonate and polyvinyl alcohol.

In one embodiment, the multilayer structure described above is assembled together and disposed between a first release liner 32 and a second release liner 34. In one embodiment, the first release liner 32 desirably overlies the first absorbable adhesive film 28A and the second release liner 34 desirably overlies the layer of an absorbable material 30. The first and second release liners may include release paper such as that sold commercially by Tekkote Corporation of Leonia, N.J. The structure between the first and second release liners 32, 34 may be subjected to pressure and heat to laminate the support layer 22 with the layer of an absorbable material 30. After the lamination step, the release liners are preferably removed from the structure before the composite prosthetic device is positioned over a surface, such as an abdominal wall.

During the laminating step, pressure may be applied to the stacked layers using heated platens 36A, 36B. In one embodiment, the first platen 36A is set to a temperature of about 125-150° C. and more preferably about 140° C., and the second platen 36B is set to a temperature of about 130-160° C. and more preferably about 145° C. The pressure applied to the stacked layers by the closed platens 36A, 36B may be about 50-100 psi and more preferably about 75 psi. In one embodiment, the first and second platens 36A, 36B are closed for about 30 seconds to apply heat and pressure to the stacked assembly. After heat and pressure are applied, the laminated assembly is desirably removed from the press and allowed to cool at room temperature for a period of time, such as about one minute or more.

After cooling, the two release liners 32, 34 may be removed, and the laminated assembly may be placed into a second, unheated press. In the second, unheated press, the platens or rollers applying the pressure are preferably maintained at room temperature. The laminate may be pressed in the cold press for about 15 seconds at about 55 psi. In one embodiment, the unheated, second pressure step is conducted with the second absorbable material 30 being oriented face up relative to the support layer 22.

In one embodiment, the unheated press includes an air press equipped with platens covered with silicone rubber with a thin polyurethane covering film placed over the silicone rubber. In one embodiment, the laminated assembly is allowed to cool for about three minutes after the heated laminated step before being subjected to the unheated, second press step. In other embodiments, rollers such as compliant rollers may be used for laminating the layers together. In one embodiment, the assembled stack is laminated together using pressure and heat. The laminated stack is then allowed to cool at room temperature, and is again pressed at room temperature using unheated platens or rollers.

In one embodiment, the materials used in the laminate are pre-cut to a desired size and shape, such as a size and shape that will fit the first and second platens 36A, 36B. The materials may be cut using well-known cutting tools, such as dies. Before the lamination step, the cut materials are preferably assembled into a multilayer stack, such as in the order shown in FIG. 1. In one embodiment, the second release liner 34 is stripped from both sides of a 0.8 mil absorbable adhesive film (e.g. PDS) and the second release liner 34 is placed atop the second platen 36B with the release side facing up. The layer of an absorbable material 30 (e.g. ORC) is placed over the second release liner 34, and the second absorbable adhesive film 28B is positioned over the layer of an absorbable material 30. A support layer 22, such as a piece of PROLENE® Soft Mesh (PSM), is placed over the second absorbable adhesive film 28B, and the first absorbable adhesive film 28A is placed over the support layer 22. The first release liner 32 covers the first absorbable adhesive film 28A. The first absorbable adhesive film 28A and the first release liner 32 are oriented so that the first absorbable adhesive film confronts the top surface 24 of the support layer 22.

In one embodiment, before the lamination step, one or more of the layers in the stack is exposed to moisture or humidity to increase the moisture content thereof. As will be described in more detail herein, it has been discovered that increasing the moisture content of one or more of the layers will improve the bond strength between the layers. In one embodiment, the layer of an absorbable material 30 (e.g. a cellulose fabric such as ORC) is exposed to moisture, or elevated relative humidity, or is pre-hydrated prior to being laminated with the support layer 22 (e.g. a PSM layer). As a result, the layer of an absorbable material 30 has a higher moisture content than it would if stored at ambient conditions, which enhances heat transfer throughout the assembly during the laminating step.

Figure 2:
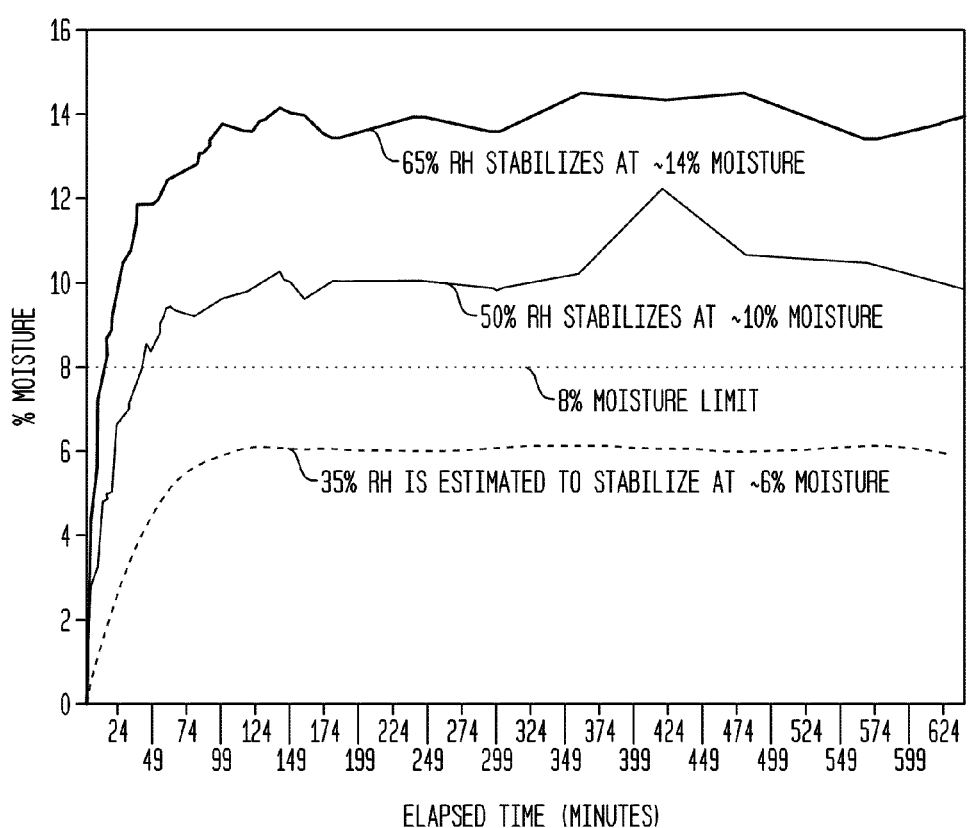
FIG. 2 is a graph showing the moisture content of a material versus exposure times at 35%, 50%, and 65% relative humidity, in accordance with one embodiment of the present invention.

It has been observed that cellulosic fabrics such as ORC fabric will absorb moisture and will reach a point of equilibrium in response to the surrounding environmental conditions. As shown in the graph in FIG. 2, when the cellulosic fabric is exposed to various humidity levels for a period of time, such as about two (2) hours, the fabric reaches a saturation point. In FIG. 2, the saturation point is indicated by the plateau that is reached within the plots for the various relative humidity levels. At 35% relative humidity, the ORC fabric stabilizes at about 6% moisture content. At 50% relative humidity, the ORC fabric stabilizes at about 10% moisture content. At 65% relative humidity, the ORC fabric stabilizes at about 14% moisture content. Other fabrics and materials may respond most effectively to different relative humidity, temperature and exposure time levels and still fall within the scope of the present invention.

In one embodiment, before the lamination steps, one or more layers of the laminate are preferably held in a storage unit having a nitrogen atmosphere. The storage unit is preferably maintained with a continuous nitrogen flow of 12 SCFH (Standard Cubic Feet per Hour). Between process steps, exposure of the layers to atmospheric conditions is preferably minimized. The storage unit may also provide UV protection for the layers of the laminate. The one or more layers stored in the storage unit may not be subjected to higher relative humidity before the laminating step.

As shown in FIG. 3, in one embodiment of the present invention, the strength of the bonds between the laminated layers is significantly improved by introducing moisture into the system immediately prior to lamination. This "bond strengthening" effect is counter-intuitive to the expected norms associated with processing absorbable polymer systems. Traditionally, it is expected that the mechanical properties of an absorbable polymer will degrade in the presence of moisture. It is clear from the data presented in FIG. 3, however, that the opposite is the case. Although the present invention is not limited by any particular theory of operation, it is believed that the increased bond strength is attributable to the elevated moisture content of at least one of the layers in the assembly, and is particularly attributable to the elevated moisture content of the ORC material prior to lamination. The elevated level of moisture in the ORC material during lamination increases the heat transfer capabilities of the laminating tools (e.g. a heat press). Moreover, it is believed that much of the moisture present in the ORC material is vaporized during the lamination process.

In one embodiment, bond strength testing was conducted on the above-described laminated materials using an Instron tensile test unit. As shown in FIG. 4, strips of the laminated material were cut at approximately 1" wide along the wale direction of the support layer. A test tab was made in the cut strips by peeling approximately one inch of the end of the laminated strip for placement in the grips of the Instron unit. The Instron was set-up using the following parameters: 1) gauge length 0.25 in.; 2) crosshead speed=20 in./min. as defined by the Instron software setting; 3) load cell capacity=5 lb. or 10 lb. with Instron 3343; and 4) grip pressure setting=60 psi. The average force between two crosshead displacements was calculated and is reported as the average bond strength. Samples were tested immediately after preparation or were kept in a nitrogen or vacuum environment until testing to prevent degradation of the absorbable components. Testing was performed under ambient environmental conditions. The laminated strips were placed in the Instron grips with the base of the ORC fabric loops oriented towards the upper platen of the Instron. The gauge length was zeroed and the load cell was rebalanced prior to attaching a test sample if the load on the display exceeded 0.0050 lbs. or was less than −0.0050 lbs.

The more flexible tab (e.g. ORC layer) was placed in the bottom grip, and the polypropylene mesh was placed in the upper grip. After the movable grip was started in motion, the values obtained through the first ½ inch of the strip were disregarded. The average force detected during testing of the next two inches of the strip was recorded as the bond strength. The test results, shown in graphical form in FIG. 3, indicate that the bond strength of the laminated layers is directly related to the relative humidity level to which the ORC material is exposed. In one embodiment, the optimum bond strength is achieved at 86% relative humidity, and the bond strength drops slightly between 86% relative humidity and liquid dousing of the ORC.

The moisture content in the cellulosic fabric before the lamination step may be determined through the use of a method commonly referred to as a "loss on drying" (L.O.D.) method. In this method, the weight of the sample is recorded prior to the test, and the weight is again recorded after the material has been exposed to an elevated temperature "drying" cycle. The difference between the starting weight and the final post drying weight is divided by the initial weight and the value is reported as a percentage weight loss.

FIG. 5 plots the bond strength of the bond between the laminated layers versus the loss on drying values. In one embodiment, loss on drying testing (LOD) was conducted by preparing test samples under nitrogen. In one step, weighing bottles and covers were dried in an oven at 90° C. for one hour. The hot, dry weighing bottles (with their airtight covers on) were placed in a desiccator or nitrogen box to cool to room temperature. Afterwards, the cool weighing bottles were placed in the nitrogen bag or glove box and weighed. The weight was recorded to the nearest 0.0001 g. The material samples were immediately placed in a nitrogen bag or glove box, which was previously purged. The sample packages were opened under nitrogen and the samples were cut into the appropriate size. The cut laminate or fabric samples were placed into the weighing bottles. Approximately 0.5 g to 1.0 g of sample was placed into the weighing bottle and the lid was applied. The weighing bottles containing the samples were then weighed inside the nitrogen bag or glove box. They were weighed to the nearest 0.0001 g and the weights were recorded. The weighing bottles with the lids closed were removed from the nitrogen bag or glove box. The weighing bottles, with the covers open, were placed in an oven at 90° C. for 1 hour to dry the sample. After one hour, the covers were replaced on the weighing bottles and the bottles were carefully moved to a desiccator or nitrogen box for cooling. After the weighing bottles cooled to room temperature in the desiccator or nitrogen box, they were weighed to the nearest 0.0001 g and the weights were recorded. The Percent Loss On Drying was calculated as:

$$L = \frac{W - R}{W} \times 100$$

wherein, L=percent loss on drying, R=weight of dried residue in grams, and W=sample weight in grams. The laminated devices that lost the most weight (or moisture) during the lamination process had the highest bond strength, thereby providing evidence that there is a strong link between elevated moisture content and increased bond strength.

In one embodiment, in the pre-lamination condition, ORC material has a moisture content of approximately 12%. After lamination, the laminated composite structure demonstrated an average loss on drying value of approximately 1.4%. While both values have been reported as determined, they are not directly equivalent. This is because the ORC component of the composite structure accounts for approximately 50% of the total mass of the laminate. As such, it is appropriate to multiply the reported laminate loss on drying value by 2 to determine the true moisture content of the ORC component of the laminate. The result indicates that the average moisture content of the ORC component of the final laminate is approximately 2.8%, far less than the 12% moisture content of the materials in the starting condition. Thus, the above testing confirms that the moisture in the ORC material is vaporized during lamination.

Figure 6:
FIG. 6 shows a microscopic view of a conventional composite structure as the layers of the structure are pulled apart.

In another experiment, optical microscopy was used to study laminated structures produced with materials pre-stored in ambient conditions vs. laminated structures produced with materials that were subjected to elevated moisture levels prior to lamination. During this experiment, the layers of the samples were pulled apart under direct visualization. FIG. 6 shows a laminated structure in which the component parts were stored at ambient conditions prior to the lamination process. As shown in FIG. 6, the laminate structure is held together through tacking of a 0.0002" PDS film to a 0.0008" PDS film in a strap-like fashion in the open interstices of the polypropylene fabric (e.g. see the portion within the circle). As the laminated structure is pulled apart, the 0.0002" thick straps are severed/sheared from the attachment to the 0.0008"/ORC laminate.

Figure 7:
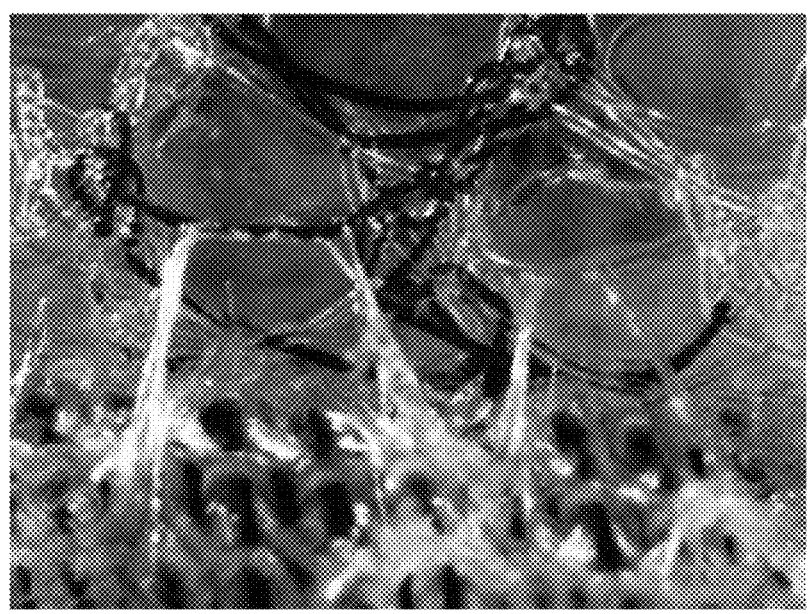
FIG. 7 shows a microscopic view of a composite prosthetic device as the layers of the device are pulled apart, in accordance with one embodiment of the present invention.

FIG. 7 shows a laminated structure made using the present invention whereby one or more of the components of the structure is exposed to elevated relative humidity levels or increased moisture content prior to the lamination step. In FIG. 7, it can be seen that the absorbable adhesive films bond directly to the fibers of the support layer (e.g. polypropylene fabric) and when pulled apart, the absorbable adhesive film materials must tear in a string-like fashion from the individual fibers, including the 0.0008" thick PDS film. In contrast to the structure shown in FIG. 6, the PDS polymer in the present invention appears to be fully integrated into the support layer and the 0.0008" film layer must fail before allowing the polypropylene fabric to separate from the ORC fabric. Thus, the bond strength of the laminate shown in FIG. 7 is significantly greater than the bond strength of the laminate shown in FIG. 6.

It is believed that the above-described methods for making medical devices having improved bond strength, supported by the above experimental data, provide a significant advance over conventional methods of laminating materials. Increasing the humidity level or the moisture content of the materials may be achieved easily and inexpensively, such as by using environmental chambers in production areas. Such a minor change in the production process, however, results is a final product that displays a tremendous improvement in bond strength.

Figure 8:
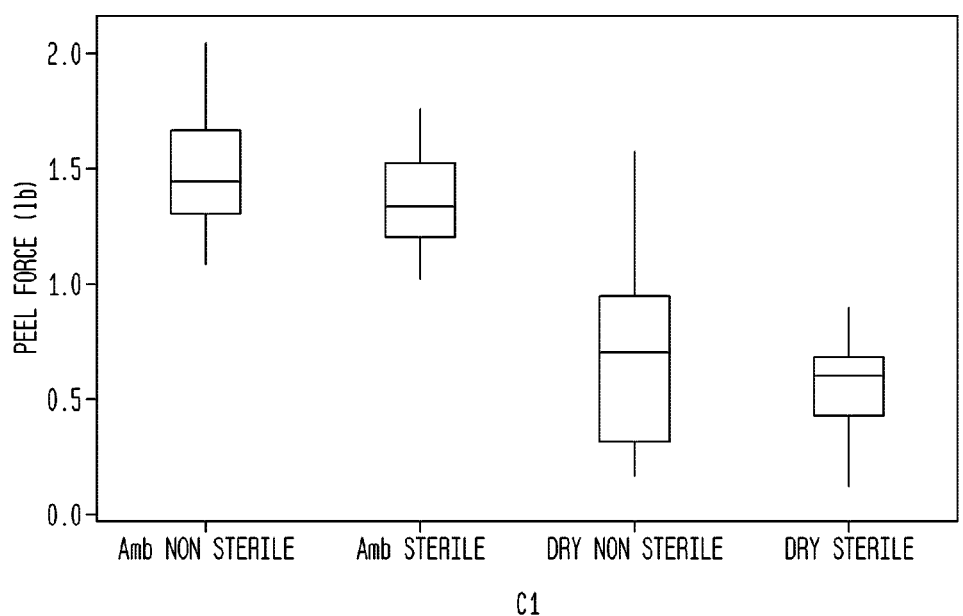
FIG. 8 is a graph showing a comparison of the bond strength of composite structures having materials pre-stored at ambient conditions versus pre-dried materials.

It has also been observed that the bond strength of a laminated, composite prosthetic device is negatively impacted by the removal of moisture from one of the layers of the device prior to lamination. In one embodiment, the storage conditions for all of the layers used in the laminate remain constant with the exception being that a first group of materials (e.g. a first set of ORC layers) is stored in ambient conditions overnight, and a second group of materials (e.g. a second set of ORC layers) is dried in a vacuum chamber overnight. The two different groups of the materials are then removed from the different storage environments (ambient conditions v. dry vacuum chamber) and used to make composite prosthetic devices. The results, shown in graphical form in FIG. 8, indicate that the bond strength for medical devices made using the first set of materials (e.g. the ORC stored in ambient conditions) is greater than the bond strength for medical devices made using material subjected to drying (e.g. the ORC pre-dried in a vacuum chamber). The weakening of the bond strength occurred in both sterile and non-sterile environments. In one embodiment, one or more of the remaining layers in the composite device may be pre-stored in a nitrogen environment prior to the lamination step. In more preferred embodiments, the absorbable adhesive film is stored in a nitrogen chamber prior to the lamination step.

In one embodiment of the present invention, a composite prosthetic device may be assembled by joining the support layer 22, the absorbable adhesive 28A, 28B, and the layer of an absorbable material 30 using pressure and heat. Other assembly techniques may include using pressure and heat along with stitching, tacking, lamination, compression heating, laser welding, sonic welding or using adhesive.

Figure 9:
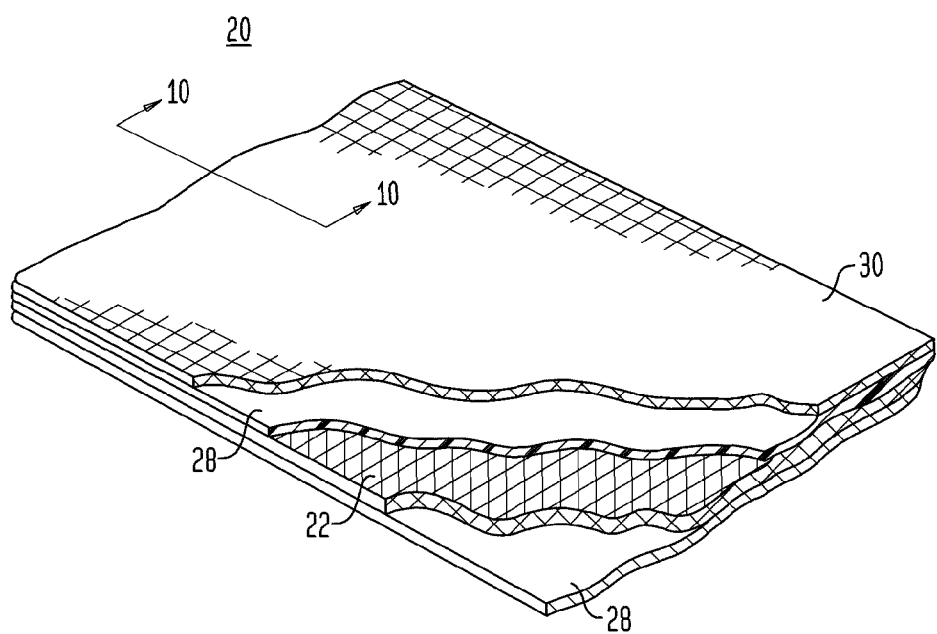
FIG. 9 shows a perspective view of a composite prosthetic device, in accordance with one embodiment of the present invention.
Figure 10:
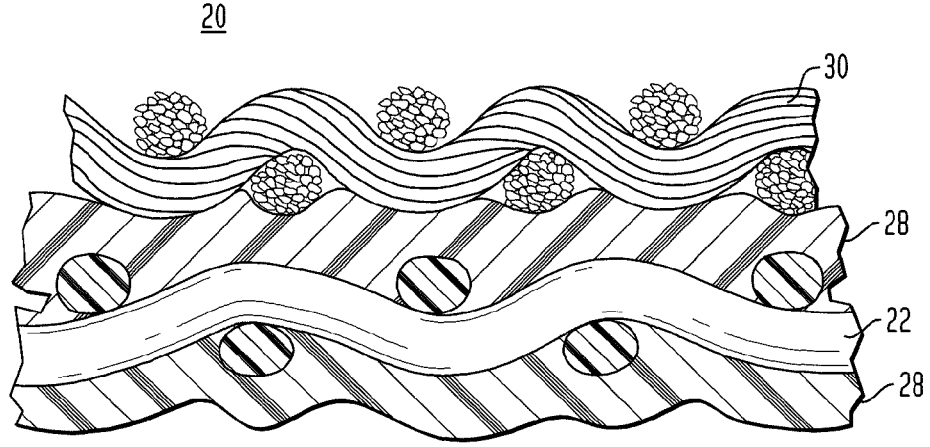
FIG. 10 shows a cross-sectional view of the composite prosthetic device of FIG. 9 taken along line X-X thereof.

FIGS. 9 and 10 show a composite prosthetic device 20 made using one or more of the steps disclosed. The device 20 preferably includes a support layer 22 such as a layer of a polypropylene mesh (PSM), and an absorbable adhesive 28 that coats the support layer 22. The composite prosthetic device includes a layer of an absorbable material 30 such as a layer of cellulosic fabric. The absorbable adhesive 28 desirably joins the support layer 22 to the layer of an absorbable layer 30. In one embodiment, the absorbable adhesive 28 has a melting point that is lower than the melting point of either the support layer 22 or the layer of an absorbable material 30. In one embodiment of the present invention, a composite prosthetic device 20 may include one or more layers of the support layer 22 (e.g. PSM), one or more layers of the absorbable adhesive 28 (e.g. PDS), and one or more layers of the absorbable material 30 (e.g. ORC).

In one embodiment, the support layer 22 provides strength to the composite prosthetic device. Moreover, after the absorbable adhesive 28 has been sufficiently absorbed, some of the pores of the support layer 22 may become exposed, to allow tissue in-growth into the support layer 22. The layer of the absorbable material 30 may isolate the support layer 22 from the internal or abdominal viscera or tissue and organs for a period of time after implantation. The layer of the absorbable material 30 may also function as an adhesion barrier to prevent postoperative adhesions between the support layer 22 and the internal or abdominal viscera. In one embodiment, the layer of an absorbable material 30 may have a faster absorption rate than the absorption rate of the absorbable adhesive 28A, 28B.

In certain preferred embodiments of the present invention, the prosthetic repair devices described herein may incorporate therein one or more therapeutic agents, including but not limited to antimicrobial agents such as 2,4,4'-trichloro-2'hydroxydip-henyl ether, benzalkonium chloride, silver sulfadiazine, povidone iodine, triclosan, gentamiacin; anti-inflammatory agents, steroidal or non-steroidal, such as celecoxib, rofecoxib, aspirin, diclofenac, salicylic acid, acetominophen, indomethicin, sulindac, tolmetin, ketorolac, mefanamic acid, ibuprofen, naproxen, phenylbutazone, sulfinpyrazone, apazone, piroxicam, anesthetic agents such as channel blocking agents, lidocaine, bupivacaine, mepivacaine, procaine, chloroprocaine, ropivacaine, tetracaine, prilocaine, levobupivicaine, and combinations of local anesthetics with epinephrine etc., anti-proliferatives such as rapamycin, growth factors such as PGDF, scar treatment agents such as hylauronic acid, angio-genesis promoting agents, pro-coagulation factors, anti-coagulation factors, chemotactic agents, agents to promote apoptosis, immunomodulators, mitogenic agents, diphenhydramine, chlorpheniramine, pyrilamine, promethazin, meclizine, terfenadine, astemizole, fexofenidine, loratidine, aurothioglucose, auranofin, Cortisol (hydrocortisone), cortisone, fludrocortisone, prednisone, prednisolone, 6.alpha.-methylprednisone, triamcinolone, betamethasone, and dexamethasone; hemostatic agents such as thrombin, tranexamic acid, and epinephrine, as well as antiviral and antithrombotic agents.

In one embodiment of the present invention, the composite prosthetic devices may be used for the repair of hernias and other fascial deficiencies. The techniques used for the repair of a hernia may vary considerably. For example, the composite prosthetic device may be placed intraperitoneally, either via open or laparoscopic surgery. Alternatively, the composite prosthetic device may be placed extraperitoneally below or under the rectus muscle, via open or laparoscopic surgery. In other embodiments, the composite prosthetic device may be used to repair a hernia or fascial defect using an onlay technique, whereby the device is placed above or on top of the rectus muscle, or by using a subfascial technique.

While the foregoing is directed to embodiments of the present invention, persons skilled in the art will recognize that other and further embodiments of the invention may be devised without departing from the basic scope thereof. These additions and/or alterations are considered to be equivalents of the present invention.

What is claimed is:

1. A method of making a composite prosthetic device comprising:
    providing a support layer;
    juxtaposing a layer of an absorbable material with said support layer;
    disposing an absorbable adhesive between said support layer and said layer of an absorbable material;
    heating said layers for melting said absorbable adhesive;
    increasing the moisture content of at least one of said layers for improving thermal conduction between said layers; and
    after the heating step, cooling said absorbable adhesive to form a structural bond of said absorbable adhesive to said juxtaposed layers.

2. The method as claimed in claim 1, wherein the increasing the moisture content step occurs prior to the heating step, and wherein after the cooling step said absorbable adhesive is reflowable upon reheating said absorbable adhesive.

3. The method as claimed in claim 1, wherein the increasing the moisture content step occurs during the heating step.

4. The method as claimed in claim 1, wherein the increasing the moisture content step includes exposing the at least one of said layers to an environment having an elevated humidity level relative to ambient conditions.

5. The method as claimed in claim 4, wherein the exposing step includes placing the at least one of said layers inside an enclosed area that has the elevated humidity level relative to the ambient conditions.

6. The method as claimed in claim 4, wherein the at least one of said layers is exposed to the elevated humidity level for at least one hour before the heating step.

7. The method as claimed in claim 4, wherein the at least one of said layers is exposed to the elevated humidity level for about two hours before the heating step.

8. The method as claimed in claim 4, wherein the elevated humidity level is between about 70-86% relative humidity.

9. The method as claimed in claim 1, further comprising applying pressure to said layers during the heating step.

10. The method as claimed in claim 9, wherein the applying pressure step includes using platens or rollers to compress said layers, and wherein the method further comprises introducing water, moisture, or steam to said layers through openings in said platens or rollers.

11. The method as claimed in claim 1, wherein said support layer comprises a polypropylene mesh, said layer of an absorbable material comprises oxidized regenerated cellulose, and said absorbable adhesive comprises a polydioxanone film.

12. A method of making a composite prosthetic device comprising:
    providing a support layer;
    juxtaposing a layer of an absorbable, anti-adhesion material with said support layer;
    disposing an absorbable adhesive between said support layer and said layer of an absorbable, anti-adhesion material;
    heating said absorbable adhesive for bonding said support layer with said layer of an absorbable, anti-adhesion material;
    prior to the heating step, increasing the moisture content of at least one of said layers for improving thermal conductivity during the heating step; and
    after the heating step, cooling said absorbable adhesive to form a structural bond of said absorbable adhesive to said juxtaposed layers.

13. The method as claimed in claim 12, wherein the increasing the moisture content step comprises:
    storing the at least one of said layers inside an enclosed area having an elevated humidity level for at least one minute; and
    removing the at least one of said layers from the enclosed area before the heating step.

14. The method as claimed in claim 12, further comprising applying pressure to said layers during the heating step.

15. The method as claimed in claim 12, wherein said support layer comprises polypropylene mesh, said layer of an absorbable, anti-adhesion material comprises cellulose fabric, and said absorbable adhesive comprises a thermoplastic adhesive film that is reflowable after the cooling step upon reheating said absorbable adhesive.

16. The method as claimed in claim 12, further comprising providing a second absorbable adhesive over a surface of said support layer facing away from said layer of an absorbable, anti-adhesion material.

17. A method of making a composite prosthetic device comprising:
    assembling a multilayer structure including
        a first support layer having a first surface and a second surface;
        a second layer of an absorbable adhesive overlying the first surface of said first layer;
        a third layer of an absorbable adhesive overlying the second surface of said first layer;
        a fourth layer of an absorbable material overlying said third layer of an absorbable adhesive;
    heating said assembled multilayer structure to melt said second and third layers of an absorbable adhesive so as to bond said first and fourth layers together;
    prior to the heating step, increasing the moisture content of at least one of said layers for improving thermal conductivity throughout said assembled multilayer structure during the heating step; and
    after the heating step, cooling said device to form a structural bond of said absorbable adhesive to said first support layer and said fourth layer of an absorbable material.

18. The method as claimed in claim 17, wherein said first support layer has openings therein, and wherein said absorbable adhesive flows into said openings during the heating step to form an absorbable barrier coating said first and second surfaces of said first support layer.

19. The method as claimed in claim 17, further comprising applying pressure to said assembled multilayer structure during the heating step.

20. The method as claimed in claim 17, wherein the increasing the moisture content step comprises exposing said fourth layer of an absorbable material to an elevated humidity level prior to the heating step.

21. The method as claimed in claim 17, wherein the increasing the moisture content step comprises exposing at least one of said layers to an enclosed environment having an elevated humidity level.

22. The method as claimed in claim 21, wherein the exposing step comprises storing the at least one of said layers inside the enclosed environment having an elevated humidity level for at least one minute, and removing the at least one of said layers from the environment prior to the assembling and heating steps.

23. The method as claimed in claim 22, wherein the elevated humidity level is between about 70-86% relative humidity.

24. The method as claimed in claim 19, further comprising prior to the heating and pressure steps, disposing a first release liner over said second layer of an absorbable adhesive and a second release liner over said fourth layer of an absorbable adhesive.

25. The method as claimed in claim 17, wherein said first support layer comprises polypropylene, said second and third layers of an absorbable adhesive comprise a thermoplastic adhesive that is reflowable after the cooling step by reheating said absorbable adhesive, and said fourth layer of an absorbable material comprises cellulose fabric.

* * * * *